United States Patent [19]

Callery et al.

[11] Patent Number: 5,612,329
[45] Date of Patent: Mar. 18, 1997

[54] DIAZIRIDINYLPOLYAMINE ANTI-CANCER AGENTS

[75] Inventors: Patrick S. Callery, Perry Hall; Merrill J. Egorin, Reisterstown; Yanglong Li, Dundalk, all of Md.; Zhi-min Yuan, Brookline, Mass.

[73] Assignee: University of Maryland at Baltimore, Baltimore, Md.

[21] Appl. No.: 462,636

[22] Filed: Jun. 5, 1995

[51] Int. Cl.$^6$ ...................... A61K 31/395; C07D 403/12
[52] U.S. Cl. ............................................. 514/183; 548/962
[58] Field of Search ............................. 514/183; 548/962

[56] References Cited

PUBLICATIONS

Hartley et al, "An Agarose Gel Method for the Determination of DNA Interstand Crosslinking Applicable to the Measurement of the Rate of Total and Second–Arm Crosslink Reactions", *Analytical Biochemistry*, 193:131–134 (1991).

Byers et al, "Properties and Physiological Function of the Polyamine Transport System", *Am. J. Physiol.*, 257(Cell Physiol. 26):C545–C553 (1989).

Monks et al, "Feasibility of a High–Flux Anticancer Drug Screen Using a Diverse Panel of Cultured Human Tumor Cell Lines", *J. Natl. Cancer Inst.*, 83(11):757–766 (1991).

Porter et al, "Aliphatic Chain Length Specificity of the Polyamine Transport System in Ascites L1210 Leukemia Cells", *Cancer Res.*, 44:126–128 (1984).

Porter et al, "Biological Properties of $N^4$–Spermidine Derivatives and Their Potential in Anticancer Chemotherapy", *Cancer Res.*, 42:4072–4078 (1982).

Yuan et al, "Cytotoxicity of Aziridinyl Analogues of Polyamines Against L1210 and HL60 Cells", Abstract 2264, American Association of Cancer Researchers, Orlando, Florida (May 20, 1993) p. 380.

Lee et al, "DNA Interactions with Aziridinyl Analogues of Polyamides", Abstract (94.65), Student Research Form, p. 38, (Aug. 10, 1994) University of Maryland Medical Center, 17th Annual Medical Science Research Day–1994.

Li et al, "In Vivo Evaluation of Bisaziridinylspermine in a Murine L1210 Model", Abstract (2313), *Experimental Therapeutics*, Proceedings of the American Association for Cancer Research, 36:388 (1995) p. 388.

Rosen et al, "Cytotoxicity and Cellular Pharmacology of Bisaziridinylspermine", Abstract (2314) *Experimental Therapeutics*, Proceedings of the American Association for Cancer Research, 36:388 (1995) p. 388.

Ballesteros et al, "L1210 Cell Spermidine Transport: Structure–Function Relationships Among Polyamine Analogous", Abstract (3017), *Molecular Biology/Biochemistry*, Proceedings of the American Association for Cancer Research, 36:507 (1995).

Simon et al, "Cellular Pharmacology of a Polyamine analogue", Abstract (94.09), 17th Annual Medical Science Research Day–1994, p. 8 (Aug. 10, 1995), and Poster (Sep. 14, 1994).

Cohen et al, "Targeting of Cytotoxic Agents by Polyamines: Synthesis of a Chlorambucil–Spermidine Conjugate", *J. Chem. Soc. Chem. Commun.*, pp. 298–300 (1992).

Holley et al, "Targeting of Tumor Cells and DNA by a Chlorambucil–Spermidine Conjugate", *Cancer Res.*, 52:4190–4195 (1992).

Nagarajan et al, "Chemistry of Naturally Occurring Polyamines. 10.$^1$ Nonmetabolizable Derivatives of Spermine and Spermidine", *J. Org. Chem.*, 51:4856–4861 (1986).

Darcel et al, "The Antitumoral Action of Polyamine Linked Cyclophosphazenes on Human Malignant Glioma Heterografts in nu/nu Mice", *Anticancer Research*, 10:1563–1570 (1990).

Stark et al, "Synthesis and Evaluation of Novel Spermidine Derivatives as Targeted Cancer Chemotherapeutic Agents", *J. Med. Chem.*, 35:4264–4269 (1992).

Porter et al, "Relative Abilities of Bis(ethyl) Derivatives of Putrescine, Spermidine, and Spermine to Regulate Polyamine Biosynthesis and Inhibit L1210 Leukemia Cell Growth", *Cancer Res.*, 47:2821–2825 (1987).

Heston et al, "Cytotoxic Activity of Aziridinyl Putrescine Enhanced by Polyamine Depletion with Alpha–Difluoromethylornithine", *Biochem. Pharm.*, 34(13):2409–2410 (1985).

Callery et al, "Synthesis and Antitumor Evaluation of a Highly Potent Cytotoxic DNA Cross–linking Polyamide Analogue, 1,12–Diaziridinyl–4,9–Diazadodecan", Abstract (028), American Chemical Society, Division of Medicinal Chemistry, 209th ACS National Meeting, Anaheim, California (Apr. 2–6, 1995) (no pg. #).

Tabor et al, "Polyamines", *Ann. Rev. Biochem.*, 53:749–790 (1984).

Pegg, "Polyamine Metabolism and Its Importance in Neoplastic Growth and as a Target for Chemotherapy", *Cancer Research*, 48:759–774 (1988).

Seppänen, "Some Properties of thePolyamineDeprivation–Inducible Uptake System for Methylglyoxal Bis(guanylhydrazone) in Tumor Cells", *Acta Chemica Scandinavica B*, 35:731–736 (1981).

Hemminki et al, "Correlations of Alkylating Activity and Mutagenicity in Bacteria of Cytostatic Drugs", *Acta Pharmacol et Toxicol*, 53:421–428 (1983).

Musser et al, "Alkylation of DNA with Aziridine Produced During the Hydrolysis of N,N', N"–Triethylenethiophosphoramide", *Chem. Res. Toxicol.*, 5(1):95–99 (1992).

Metzler, "DNA Adducts of Medicinal Drugs: Some Selected Examples", *J. Cancer Res. Clin. Oncol.*, 112:210–215 (1986).

Farmer, "Metabolism and Reactions of Alkylating Agents", *Pharmac. Ther.*, 35:301–358 (1987).

(List continued on next page.)

*Primary Examiner*—Jacqueline Haley
*Attorney, Agent, or Firm*—Sughrue, Mion, Zinn, Macpeak & Seas

[57] ABSTRACT

Diaziridinylpolyamines useful as anti-cancer agents; compositions containing the same, and methods of using the same for the treatment of cancer are described.

25 Claims, No Drawings

PUBLICATIONS

Heston et al, "Cytotoxic and Non–cytotoxic N–alkyl Derivatives of Putrescine: Effect on Polyamine Uptake and Growth of Prostatic Cancer Cells In Vitro", *Biochemical Pharmacology*, 36(11):1849–1852 (1987).

Piper et al, "S–2–(ω–Aminoalkylamino)ethyl Dihydrogen Phosphorothioates and Related Compounds as Potential Antiradiation Agents", *Potential Antiradiation Agents*, 12:236–243 (Mar. 1969).

O'Sullivan et al, "Molecular Features Necessary for the Uptake of Diamines and Related Compounds by the Polyamide Receptor of Rat Lung Slices", *Biochemical Pharmacology*, 41(12):1839–1848 (1991).

Dueymes et al, "Modulation of Polyclonal Activation of Lymphocytes by Cytophosphazenic Compounds Bearing Ethylene–Imino Groups and Vectorized by Polyamines", *Int. J. Immunopharmac.*, 12(5):555–560 (1990).

Yuan et al, "Cytotoxic Activity of $N^1$– and $N^8$–Aziridinyl Analogs of Spermidine", *Biochemical Pharmacology*, 47(9):1587–1592 (1994).

Hyyönen et al, "Characterization of a COS Cell Line Deficient in Polyamine Transport", *Biochemica et Biophysica Acta*, 1221:279–285 (1994).

Lakanen et al, "α–Methyl Polyamines: Metabolically Stable Spermidine and Spermine Mimics Capable of Supporting Growth in Cells Depleted of Polyamines", *J. Med. Chem.*, 35:724–734 (1992).

Boyd et al, "Some Practical Considerations and Applications of the National Cancer Institute In Vitro Anticancer Drug Discovery Screen", *Drug Development Research*, 34:91–109 (1995).

Yuan et al, "Potent Cytotoxic Aziridinyl Analogues of Polyamides", Abstract (2264), *Experimental Therapeutics*, Proceedings of the American Association for Cancer Research, 34:380 (1993).

Yuan et al, "Cytotoxic Monoaziridinylspermidines", Abstract (129), *Medi*, American Chemical Society, 204th ACS National Meeting, Washington, D.C. (Aug. 23–28, 1992) (no page No.).

DIAZIRIDINYLPOLYAMINE ANTI-CANCER AGENTS

FIELD OF THE INVENTION

The present invention relates to diaziridinylpolyamines useful as anti-cancer agents; compositions containing the same, and methods of using the same for the treatment of cancer.

BACKGROUND OF THE INVENTION

I. Polyamines

Polyamine biochemistry is believed to be intimately associated with cell growth and proliferation. This is, in part, because interference with polyamine biosynthesis and/or function can lead to cell growth inhibition or cell death (Tabor et al, *Ann. Rev. Biochem.*, 53:749–790 (1984); and Pegg, *Cancer Res.*, 48:759–774 (1988)). Further, rapidly growing tissues, such as tumors, have a high demand for polyamines, and accumulate polyamines effectively (Seppanen, *Acta Chem. Scand. B.*, 35:731–736 (1981)).

In addition, spermine and other polyamines bind avidly to DNA (Tabor et al, supra), and hence can be used to target DNA.

Thus, the polyamine homeostatic system has become a target for the design of new agents that might be concentrated in neoplastic cells and tissues via the polyamine transporter, and interact selectively with DNA.

II. Alkylating Agents

A major class of anti-cancer drugs are the alkylating agents. Alkylating agents are thought to exert tumor cell killing potency by their ability to bind and form adducts with DNA (Meltzer, *J. Cancer Res. Clin. Oncol.*, 112:210 (1986); and Farmer, *Pharmacol. Ther.*, 35:301 (1987)).

Aziridine (ethylenimine) is a ring-strained alkylating functional group that reacts covalently with cellular nucleophiles, such as DNA (Hemminki et al, *Acta Pharmacol. Toxicol.*, 53:421–428 (1983); and Musser et al, *Chem. Res. Toxicol.*, 5:95–99 (1992)). Examples of known aziridine-containing anti-cancer agents include thiotepa, mitomycin C, and diazaquone.

III. Putrescine-Based Anti-Cancer Agents

The naturally occurring polyamines, which include putrescine, spermidine and spermine, have been chemically modified to yield a number of agents that perturb polyamine biosynthesis, transport, or function (Porter et al, *Cancer Res.*, 47: 2821–2825 (1987); and Heston et al, *Biochem. Pharmacol.*, 36:1849–1852 (1987)). For example, replacement of the two amino groups of putrescine with aziridines produces the analogue, N,N'-bisaziridinyl-1,4-diaminobutane.

However, N,N'-bisaziridinyl-1,4-diaminobutane is a much less effective inhibitor of putrescine uptake than N-(4-aminobutyl)aziridine (Piper et al, *J. Med. Chem.*, 12:236–243 (1969)), wherein a single amino group of putrescine has been replaced with aziridine (O'Sullivan et al, *Biochem. Pharmacol.*, 41:1839–1848 (1991)).

N-(4-aminobutyl)aziridine has been shown to be cytotoxic against prostatic carcinoma cells (Heston et al, supra).

However, N-(4-aminobutyl)aziridine is disadvantageous because the butyl amine chain is less effective as a substrate for the polyamine transporter than the longer polyamines, such as spermine and spermidine (Byers et al, *Am. J. Physiol*, 257:C545–C553 (1989)).

IV. Spermidine-Based Anti-Cancer Agents

Chemical compounds composed of a nitrogen mustard alkylating agent covalently linked to spermidine have been found to target tumor cells and DNA (Stark et al, *J. Med. Chem.*, 35:4264–4269 (1992); Cohen et al, *J. Chem. Soc. Chem. Commun.*, 1992:298–300 (1992); and Holley et al, *Cancer Res.*, 52: 4190–4195 (1992)). In the chlorambucil-spermidine conjugate, the nitrogen mustard analogue, chlorambucil, is linked via a metabolically labile amide group and a propylamino spacer group, to the secondary amine of spermidine. Polyamine analogues which contain a nitrogen mustard alkylating group attached to the carbon alpha to the secondary amine are not substrates for the DFMO-inducible polyamine transporter (Stark et al, supra).

The above chlorambucil-spermidine conjugate is highly efficient at producing DNA cross-links compared with chlorambucil per se. However, the biological activity profile of the chlorambucil-spermidine conjugate suggests that this compound is not taken up well by cells. That is, in vivo potency does not reach the level predicted from in vitro studies.

The monoaziridinyl analogues of spermidine, $N^1$- and $N^8$-aziridinylspermidine (N-(3-aziridinylpropyl)-1,4-diaminobutane and N-(4-aziridinylbutyl)-1,3-diaminopropane have also been shown to be cytotoxic against a variety of cancer cell lines in submicromolar concentrations (Yuan et al, *Biochem. Pharmacol.*, 47:1587–1592 (1994)).

However, the above aziridinyl analogues of spermidine are disadvantageous because they do not cross-link DNA.

V. Additional Polyamine-Aziridine Anti-Cancer Agents

Polyamine-aziridine-linked cyclophosphazenes have been found to show anti-cancer activity (Darcel et al, *Anticancer Res.*, 10:1563–1570 (1990); and Dueymes et al, *Int. J. Immunopharmacol.*, 12:555–560 (1990)). These compounds consist of six-membered $N_3P_3$ rings bearing two pairs of aziridine groups bound to a phosphorus and a polyamine, such as spermidine, held in a ring structure with nitrogen-phosphorus bonds.

However, the above polyamine-aziridine-linked cyclophosphazenes are disadvantageous because the advantageous steric and electronic properties of the aziridine and polyamine moieties have been greatly altered.

SUMMARY OF THE INVENTION

An object of the present invention is to provide compounds containing aziridine moieties linked directly to polyamine moieties.

Another object of the present invention is provide compounds that are accumulated in cancer cells, are cytotoxic against cancer cells, bind to DNA, and inhibit DNA, RNA and/or protein synthesis in cancer cells.

Yet another object of the present invention is to provide anti-cancer compositions containing said compounds.

An additional object of the present invention is provide a method for treating cancer using said compounds.

These and other objects of the present invention, which will be apparent from the detailed description of the invention provided hereinafter, have been met, in one embodiment, by the diaziridinylpolyamines represented by formula (I):

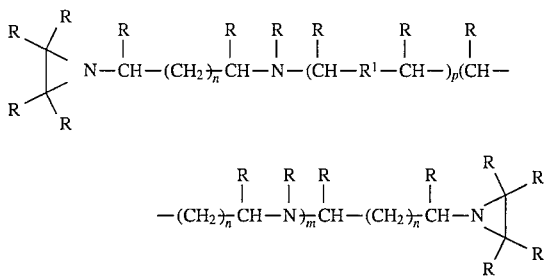

wherein each R, which may be the same or different, represents a hydrogen atom or an alkyl group having from 1 to 5 carbon atoms; $R^1$ represents CH=CH, C≡C or phenyl; each n, which may be the same or different, represents an integer of from 1 to 6; m represents 0 or an integer of from 1 to 3; and p represents 0 or an integer of from 1 to 3.

In another embodiment, the above-described objects of the present invention have been met by an anti-cancer composition comprising a pharmaceutically effective amount of a diaziridinylpolyamine represented by formula (I), and a pharmaceutically acceptable carrier or diluent.

In yet another embodiment, the above-described objects of the present invention have been met by a method for treating cancer comprising administering to a subject in need of such treatment, a pharmaceutically effective amount of a diaziridinylpolyamine represented by formula (I).

DETAILED DESCRIPTION OF THE INVENTION

As discussed above, in one embodiment, the above described objects of the present invention have been met by a diaziridinylpolyamine represented by formula (I):

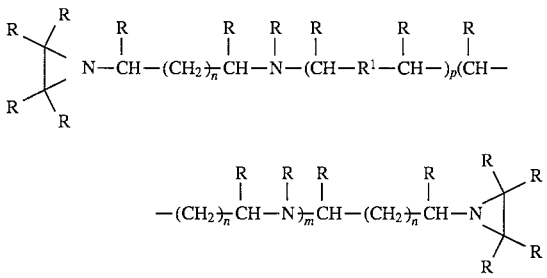

wherein each R, which may be the same or different, represents a hydrogen atom or an alkyl group having from 1 to 5 carbon atoms; $R^1$ represents CH=CH, C≡C or phenyl; each n, which may be the same or different, represents an integer of from 1 to 6; m represents 0 or an integer of from 1 to 3; and p represents 0 or an integer of from 1 to 3.

In formula (I), R is preferably a methyl, and most preferably is a hydrogen atom.

The alkyl group represented by R may be unsubstituted, or substituted with, e.g., a hydroxy group, a phenyl group, a naphthyl group or a halogen atom.

In formula (I), $R^1$ is preferably C≡C.

In formula (I), n preferably represents an integer of from 1 to 2.

In formula (I), m preferably represents 0 or an integer of from 1 to 2.

In formula (I), p preferably represents 0 or an integer of from 1 to 2.

The diaziridinylpolyamines represented by formula (I) of the present invention combine the electrophilic alkylating ability of aziridine with the carrier-meditated polyamine uptake by cancer cells associated with aminoalkyl chains.

The diaziridinylpolyamines represented by formula (I) of the present invention can be synthesized by nucleophilic addition of the appropriately substituted aziridine to acrolein or substituted acrolein. Two moles of the resulting aziridinyl aldehyde are then used to reductively alkylate one mole of the appropriately substituted alkyl diamine, alkenyl diamine, alkynyl diamine or phenylalkyl diamine, in the presence of $NaBH_4$.

As discussed above, in another embodiment, the above-described objects of the present invention have been met by an anti-cancer composition comprising a pharmaceutically effective amount of a diaziridinylpolyamine represented by formula (I), and a pharmaceutically acceptable carrier or diluent.

Examples of such pharmaceutically acceptable diluents which can be employed in the present invention include, e.g., water, saline or, a pharmaceutically acceptable buffer having a pH 5.0 to 8.0 buffer.

Examples of pharmaceutically acceptable carriers which can be employed in the present invention include 5.0% (w/v) dextrose.

In yet another embodiment, the above-described objects of the present invention have been met by a method for treating cancer comprising administering to a subject in need of treatment, a pharmaceutically effective amount of a diaziridinylpolyamine represented by formula (I).

The particular mode of administration of the diaziridinylpolyamine represented by formula (I) of the present invention is not critical. Intravenous administration is preferred.

The particular amount of the diaziridinylpolyamine represented by formula (I) to be administered in accordance with the present invention varies depending upon the mode of administration, the cancer to be treated, whether administered alone or in combination with other drugs, and the age, weight and sex of the subject to be treated. Generally, the amount to be administered intravenously is in the range of about 0.05 to 0.5 mg per kg body weight, preferably about 0.1 to 0.25 mg per kg body weight.

The cancers on which the diaziridinylpolyamines of the present invention exhibit a pharmaceutical effect are not particularly limited. However, the diaziridinylpolyamines of the present invention are particularly effective against leukemias, as well as lung, central nervous system (CNS) and renal tumors.

The following examples are provided for illustrative purposes only and are in no way intended to limit the scope of the present invention.

SYNTHESIS EXAMPLE 1

1,12-Diaziridinyl-4,9-diazadodecane 3.72 g aziridine (86.5 mmol) was dissolved in 30 ml of diethyl ether, and the resulting solution was added slowly to a solution of 4.60 g acrolein (82.1 mmol) dissolved in 20 ml of diethyl ether, while cooling in an ice bath. After stirring for 1 hr at 4° C., the mixture was concentrated on a rotary evaporator to yield 7.28 g of crude 3-aziridinylpropanal (89% yield).

1.60 g of the resulting crude 3-aziridinylpropanal (16.2 mmol) was dissolved in 15 ml of methanol, and added dropwise to a solution of 0.71 g of 1,4-diaminobutane (8.1 mmol) dissolved in 20 ml of methanol. After stirring for 10 minutes at room temperature, 1.3 g of $NaBH_4$ reducing agent was added in small portions. After 6 hr, excess reducing agent was destroyed by adding 6.0N methanolic-HCl, and the reaction mixture was evaporated to near dryness.

The resulting residue was dissolved in 10 ml of water, and adjusted to pH 12 with 40% (v/v) NaOH. The resulting solution was extracted with 30 ml of diethyl ether three times. The combined organic extracts were dried over $Na_2SO_4$, and purified by fractional distillation to yield 1.07 g (52%) of 1,12-Diaziridinyl-4,9-diazadodecane:

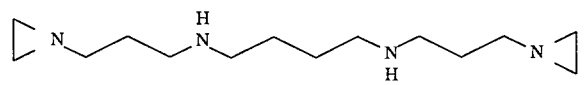

(bp 132°–134° C./0.15 mm): $^1$H NMR ($CDCl_3$) δ1.08 (m, 4H, aziridine), 1.50 (m, 4H), 1.70 (m, 4H, aziridine), 1.74 (m, 4H), 2.22 (t, 4H, J=7.5 Hz), 2.60 (m, 4H) and 2.72 (t, 4H, J=7.5 Hz) ppm; mass spectrum (EI mode) m/z 254 ($M^+$, 0.2%), 84 (100%), 42 (aziridine, 51%). Anal. ($C_{14}H_{30}N_4 \cdot 0.2$ $H_2O$) C, H, N.

Elemental analysis was within 0.4% of the theoretical empirical formula.

SYNTHESIS EXAMPLE 2

1,11-Diaziridinyl-4,8-diazaundecane 1,11-Diaziridinyl-4,8-diazaundecane, shown below, was synthesized following the procedure described in Synthesis Example 1 except that 1,3-diaminopropane was substituted for 1,4-diaminobutane in the reductive alkylation step.

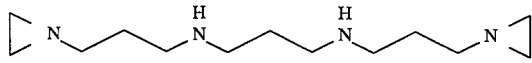

SYNTHESIS EXAMPLE 3

2,13-Diaziridinyl-5,10-diazatetradecane 2,13-Diaziridinyl-5,10-diazatetradecane, shown below, was synthesized following the procedure described in Synthesis Example 1 except that crotonaldehyde was substituted for acrolein in the nucleophilic addition step.

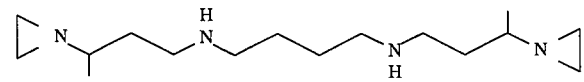

SYNTHESIS EXAMPLE 4

1,12-Di-(2-methyl-1-aziridinyl)-4,9-diazadodecane 1,12-Di-(2-methyl-1-aziridinyl)-4,9-diazadodecane, shown below, was synthesized following the procedure described in Synthesis Example 1 except that 2-methylaziridine was substituted for aziridine in the nucleophilic addition step.

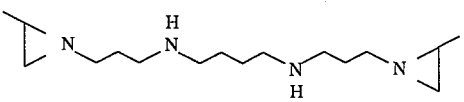

NMR and mass spectra analyses of the compounds of Synthesis Examples 1–4 were consistent with the assigned structures.

EXAMPLE 1

DNA Cross-Linking Assay 1,12-Diaziridinyl-4,9-diazadodecane, obtained in Synthesis Example 1, is a bisalkylating agent on a polyamine backbone. To determine whether this compound will cross-link DNA, 0.4 µg of pBR322 DNA was incubated at 37° C. in the presence of a 0.1 µM or 0.4 µM solution of 1,12-diaziridinyl-4,9-diazadodecane in 25 mM triethanolamine-HCl (pH 7.4) for 18 hr. For purposes of comparison, the pBR322 DNA was similarly incubated with 1.0 µM and 2.0 µM mechlorethamine, or 5.0 µM and 10.0 µM melphalan.

The test samples were then dissolved in 10 µl of strand separation buffer comprising 30% (v/v) DMSO, 1.0 mM EDTA, 0.05% (w/v) bromphenol blue and 0.04% (w/v) xylene cyanole, heated at 95° C. for 8 min, chilled immediately in a $CO_2$/ethanol bath, and then loaded onto a 0.8% (w/v) agarose gel, and subjected to agarose gel chromatography as described by Hartley et al, *Anal. Biochem.*, 193:131–134 (1991). Bands corresponding to cross-linked or double-stranded DNA and single-stranded DNA were visualized by staining the resulting gel with 0.5 µg/ml of ethidium bromide.

Nondenatured DNA and DNA denatured in the absence of test compound were used as controls.

The DNA was found to be cross-linked using diaziridinyl-4,9-diazadodecane at a concentration as low as 0.1 µM. This concentration is lower than that required for the two nitrogen mustard drugs, mechlorethamine and melphalan, to cross-link DNA.

EXAMPLE 2

In Vitro Cytotoxicity Testing in Various Cancer Cell Lines

The anti-proliferative activities of the aziridinylpolyamines obtained in Synthesis Examples 1–4 were assessed by determining $log_{10}GI50$ values against human cancer cell lines using the screening strategy described by Boyd et al, *Drug Devel. Res.* 34:91–109 (1995).

More specifically, the compounds were tested at a minimum of five concentrations at 10-fold dilutions using a 48 hr continuous exposure protocol. Each cell line shown in Table 1 below was inoculated onto microtiter plates. After a pre-incubation period of 24–48 hr at 37° C., the test compounds were added, and the culture was incubated for an additional 48 hr at 37° C. Cell viability or cell growth end-point determinations were performed by fixation of the cells, followed by staining with sulforhodamine B (Monks et al, *J. Natl. Cancer Inst.*, 83:757–766 (1991)). The results are shown in Table 1 below.

TABLE 1

Inhibition of Cell Growth Against a Panel of Human Tumor Cell Lines

| Panel/Cell Line | Synthesis Example 1 | Synthesis Example 2 | Synthesis Example 3 | Synthesis Example 4 |
|---|---|---|---|---|
| Leukemia | | | | |
| CCRF-CEN | −7.20[a] | −5.43 | −5.32 | −5.40 |
| HL-60 (TB) | −7.45 | −5.57 | −5.48 | −5.53 |
| K-562 | −5.36 | −4.71 | −4.67 | −4.53 |
| MOLT-4 | −7.35 | −5.51 | −5.49 | −5.53 |
| RPMI-8226 | −5.29 | −4.65 | −4.56 | −4.50 |
| SR | −7.74 | −5.51 | −5.44 | −5.31 |
| Non-Small Cell Lung Cancer | | | | |
| A549/ATCC | −6.05 | −4.88 | −4.53 | −4.74 |
| EKVX | −5.46 | −4.60 | −4.51 | −4.49 |
| HOP-62 | −7.23 | −5.20 | −4.51 | −4.97 |
| HOP-92 | −6.66 | −4.95 | −4.72 | −4.84 |
| NCI-H226 | −6.14 | −4.73 | −4.63 | −4.72 |
| NCI-H23 | −6.58 | −4.97 | −4.88 | −5.06 |
| NCI-H322M | −5.34 | −4.44 | −4.20 | −4.04 |
| NCI-H460 | −6.44 | −5.53 | −5.21 | −5.04 |
| NCI-H522 | −6.37 | −4.95 | −4.90 | −5.14 |
| Colon Cancer | | | | |
| COLO 205 | −6.39 | −4.88 | −4.83 | −5.00 |
| HCC-2998 | −5.74 | −4.69 | −4.26 | −4.72 |
| HCT-116 | −5.90 | −4.71 | −4.58 | −4.68 |
| HCT-15 | −4.94 | −4.66 | −4.38 | > −4.00 |
| HT29 | −5.44 | −4.73 | −4.70 | −4.69 |
| KM12 | −4.81 | −4.71 | −4.09 | −4.19 |
| SW-620 | −5.58 | −4.58 | −4.65 | −4.38 |
| CNS Cancer | | | | |
| SF-268 | −6.83 | −4.97 | −4.84 | −4.69 |
| SF-295 | −6.81 | −4.84 | −4.62 | −4.32 |
| SF-539 | −7.43 | −4.95 | −5.20 | −4.89 |
| SNB-19 | −5.95 | −4.74 | −4.58 | −4.59 |
| SNB-75 | −7.56 | −5.40 | −5.47 | −5.63 |
| U251 | −6.38 | −5.16 | −4.80 | −4.88 |
| Renal Cancer | | | | |
| 786-0 | −7.95 | −5.47 | −5.42 | −5.35 |
| A498 | −5.74 | −4.55 | −4.16 | > −4.00 |
| ACHN | −6.85 | −5.41 | −5.24 | −4.72 |
| CAKI-1 | −7.73 | −5.39 | −5.30 | −5.46 |
| RXF-393 | −6.86 | −5.41 | −4.82 | −4.96 |
| SN12C | −6.87 | −5.17 | −5.02 | −5.01 |
| TK-10 | −5.49 | −4.84 | > −4.00 | −4.93 |
| UO-31 | −6.24 | −4.77 | −4.45 | −4.76 |

[a] $\log_{10}$ GI50 values are molar concentrations achieving 50% inhibition of cell growth As shown in Table 1 above, the aziridinylpolyamines obtained in Synthesis Examples 1–4 are cytotoxic in concentrations in the nanomolar range, and that the cytotoxic response is greater for some cancer cell lines than others. Most notable, is the selectively high potency against leukemias, and lung, CNS and renal cancers.

EXAMPLE 3

In Vivo Testing in Mice

Virus-free, adult female $CD_2F_1$ mice were obtained from the Animal Genetics and Production Branch of the National Cancer Institute. To minimize exogenous infection, mice were housed in microisolator caging and handled in accordance with the NIH Guide for the care and use of laboratory animals (NIH No. 85-23, 1985). The mice were randomized to groups of 5 mice per group, except titration groups which consisted of 10 mice per group, and the untreated control group which consisted of 20 mice.

On day 0, the mice were inoculated intraperitoneally with $1.0 \times 10^5$ L1210 mouse leukemia cells/mouse for the treatment and control groups. The titration groups received $1.0 \times 10^4$ to $1.0 \times 10^6$ L1210 cells/mouse.

Dosing solutions were freshly prepared just prior to treatment by dissolving 1,12-diaziridinyl-4,9-diazadodecane in 25 mM sodium phosphate buffer (pH 7.4), giving concentrations of 0.18–0.6 mg/ml.

Beginning on day 1, dosing solutions were administered intravenously by tail vein at 0.01 ml/g of body weight. The doses of 1,12-diaziridinyl-4,9-diazadodecane were 6.0, 4.0, 2.7, and 1.8 mg/kg. The dosing schedule was: a single dose on day 1; 3 doses every four days beginning on day 1; 2 doses every seven days beginning on day 1; or 2 doses on days 1 and 2.

Tumor doubling time was calculated from the median days of death for the titration groups, and was found to be 0.3 days.

Percent increase in lifespan was calculated using the formula, (T−C/C)·100, where T is the median day of death for the various treatment groups, and C is the median day of death for the control group.

The net log cell kill is an estimate of the number of cells that are killed by the drug at each specific dose and schedule, and was calculated by the formula, ((T−C)−Duration of Treatment)·0.3/Tumor Doubling Time. The results are shown in Table 2 below.

TABLE 2

Effects of Treatment With 1,12-Diaziridinyl-4,9-diazadodecane on the Life Span of Mice Bearing L1210 Murine Leukemia

| Treatment[a] (mg/kg) | Survival[b] (days) | % ILS[c] | NLCK[d] |
|---|---|---|---|
| control | 7 | 0 | — |
| 4.0 on days 1, 5, 9 | 8 | 14 | −7[e] |
| 2.7 on days 1, 5, 9 | 19 | 171 | 4 |
| 1.8 on days 1, 5, 9 | 17 | 143 | 2 |
| 4.0 on days 1, 8 | 18 | 157 | 4[e] |
| 2.7 on days 1, 8 | 16 | 129 | 2 |
| 1.8 on days 1, 8 | 13 | 86 | −1 |
| 4.0 on days 1, 2 | 5 | −29 | −3[f] |
| 2.7 on days 1, 2 | 14 | 100 | 6[e] |
| 1.8 on days 1, 2 | 14 | 100 | 6 |
| 6.0 on day 1 | 6 | −14 | −1 |
| 4.0 on day 1 | 11 | 57 | 4[e] |
| 2.7 on day 1 | 10 | 42 | 3 |
| 1.8 on day 1 | 11 | 57 | 4 |

[a] - Intravenous dose
[b] - Median day of death
[c] - Percent increase in life span
[d] - Net log cell kill
[e] - $LD_{20}$
[f] - $LD_{100}$ As shown in Table 2 above, a significant increase in the life span of female $CD_2F_1$ mice, bearing L1210 murine leukemia, was observed after intravenous administration of 1,12-diaziridinyl-4,9-diazadodecane in doses of less than 2.7 mg/kg, given on days 1, 5, and 9 of treatment.

While the invention has been described in detail, and with reference to specific embodiments thereof, it will be apparent to one of ordinary skill in the art that various changes and modifications can be made therein without departing from the spirit and scope thereof.

We claim:

1. A diaziridinylpolyamine represented by formula (I):

$$R\!\!\diagup\!\!\!\!\diagdown\!\!\!\!\!{}^R_R\!\!\!\diagdown\!\!\!\!\!\!\!\diagup\!\!\!{}^R \;\; \underset{|}{N}-\underset{|}{\overset{R}{C}H}-(CH_2)_{\overline{n}}\underset{|}{\overset{R}{C}H}-\underset{|}{\overset{R}{N}}-(\underset{|}{\overset{R}{C}H}-R^1-\underset{|}{\overset{R}{C}H}-)_p(\underset{|}{\overset{R}{C}H}-$$

$$-(CH_2)_{\overline{n}}\underset{|}{\overset{R}{C}H}-\underset{|}{\overset{R}{N}})_{\overline{m}}\underset{|}{\overset{R}{C}H}-(CH_2)_{\overline{n}}\underset{|}{\overset{R}{C}H}-N\!\!\diagup\!\!\!\!\diagdown\!\!\!\!\!{}^R_R$$

wherein each R, which may be the same or different, represents a hydrogen atom or an alkyl group having from 1 to 5 carbon atoms; $R^1$ represents CH=CH, C≡C or phenyl; each n, which may be the same or different, represents an integer of from 1 to 6; m represents 0 or an integer of from 1 to 3 and p represents 0 or an integer of from 1 to 3.

2. The compound of claim 1, wherein R is a methyl group.

3. The compound of claim 1, wherein R is a hydrogen atom.

4. The compound of claim 1, wherein $R^1$ is C≡C.

5. The compound of claim 1, wherein n is an integer of from 1 to 2.

6. The compound of claim 1, wherein m is 0 or an integer of from 1 to 2.

7. The compound of claim 1, wherein p is 0 or an integer of from 1 to 2.

8. An anti-cancer composition comprising:

(A) a pharmaceutically effective amount of a diaziridinylpolyamine represented by formula (I):

$$R\!\!\diagup\!\!\!\!\diagdown\!\!\!\!\!{}^R_R\!\!\!\diagdown\!\!\!\!\!\!\!\diagup\!\!\!{}^R \;\; \underset{|}{N}-\underset{|}{\overset{R}{C}H}-(CH_2)_{\overline{n}}\underset{|}{\overset{R}{C}H}-\underset{|}{\overset{R}{N}}-(\underset{|}{\overset{R}{C}H}-R^1-\underset{|}{\overset{R}{C}H}-)_p(\underset{|}{\overset{R}{C}H}-$$

$$-(CH_2)_{\overline{n}}\underset{|}{\overset{R}{C}H}-\underset{|}{\overset{R}{N}})_{\overline{m}}\underset{|}{\overset{R}{C}H}-(CH_2)_{\overline{n}}\underset{|}{\overset{R}{C}H}-N\!\!\diagup\!\!\!\!\diagdown\!\!\!\!\!{}^R_R$$

wherein each R, which may be the same or different, represents a hydrogen atom or an alkyl group having from 1 to 5 carbon atoms; $R^1$ represents CH=CH, C≡C or phenyl; each n, which may be the same or different, represents an integer of from 1 to 6; m represents 0 or an integer of from 1 to 3; and p represents 0 or an integer of from 1 to 3; and (B) a pharmaceutically acceptable carrier or diluent.

9. The composition of claim 8, wherein R is a methyl group.

10. The composition of claim 8, wherein R is a hydrogen atom.

11. The composition of claim 8, wherein $R^1$ is C≡C.

12. The composition of claim 8, wherein n is an integer of from 1 to 2.

13. The composition of claim 8, wherein m is 0 or an integer of from 1 to 2.

14. The composition of claim 8, wherein p is 0 or an integer of from 1 to 2.

15. A method for treating cancer comprising administering to a subject in need of such treatment, a pharmaceutically effective amount of a diaziridinylpolyamine represented by formula (I):

$$R\!\!\diagup\!\!\!\!\diagdown\!\!\!\!\!{}^R_R\!\!\!\diagdown\!\!\!\!\!\!\!\diagup\!\!\!{}^R \;\; \underset{|}{N}-\underset{|}{\overset{R}{C}H}-(CH_2)_{\overline{n}}\underset{|}{\overset{R}{C}H}-\underset{|}{\overset{R}{N}}-(\underset{|}{\overset{R}{C}H}-R^1-\underset{|}{\overset{R}{C}H}-)_p(\underset{|}{\overset{R}{C}H}-$$

$$-(CH_2)_{\overline{n}}\underset{|}{\overset{R}{C}H}-\underset{|}{\overset{R}{N}})_{\overline{m}}\underset{|}{\overset{R}{C}H}-(CH_2)_{\overline{n}}\underset{|}{\overset{R}{C}H}-N\!\!\diagup\!\!\!\!\diagdown\!\!\!\!\!{}^R_R$$

wherein each R, which may be the same or different, represents a hydrogen atom or an alkyl group having from 1 to 5 carbon atoms; $R^1$ represents CH=CH, C≡C or phenyl; each n, which may be the same or different, represents an integer of from 1 to 6; m represents 0 or an integer of from 1 to 3; and p represents 0 or an integer of from 1 to 3.

16. The method of claim 15, wherein R is a methyl group.

17. The method of claim 15, wherein R is a hydrogen atom.

18. The method of claim 15, wherein $R^1$ is C≡C.

19. The method of claim 15, wherein n is an integer of from 1 to 2.

20. The method of claim 15, wherein m is 0 or an integer of from 1 to 2.

21. The method of claim 15, wherein p is 0 or an integer of from 1 to 2.

22. The method of claim 15, wherein said compound is administrated intravenously.

23. The method of claim 15, wherein said compound is administrated in an amount of about 0.05 to 0.5 mg per kg body weight.

24. The method of claim 23, wherein said compound is administrated in an amount of about 0.1 to 0.25 mg per kg body weight.

25. The method of claim 15, wherein said subject is afflicted with leukemia or lung, CNS or renal tumors.

* * * * *